United States Patent [19]
Weinstein et al.

[11] Patent Number: 5,941,241
[45] Date of Patent: *Aug. 24, 1999

[54] METHOD AND DEVICE FOR ORGANIZING AND COORDINATING THE COMBINED USE OF TOPICAL AEROSOLS FOR THE TREATMENT OF RESPIRATORY DISORDERS

[76] Inventors: Robert E. Weinstein, 177 Commonwealth Ave., Boston, Mass. 02116; Allan M. Weinstein, 9205 Pegasus Ct., Potomac, Md. 20854

[*] Notice: This patent is subject to a terminal disclaimer.

[21] Appl. No.: 08/855,893

[22] Filed: May 12, 1997

[51] Int. Cl.$^6$ .......................... A61M 11/00; B65D 83/04; G09F 3/00
[52] U.S. Cl. .......................... 128/200.23; 128/200.14; 206/534; 206/538; 206/828; 40/312
[58] Field of Search .................. 128/203.14, 200.23, 128/205.21, 203.12, 205.23; 206/732, 534, 538, 539, 562, 563, 564; 40/310

[56] References Cited

U.S. PATENT DOCUMENTS

| Re. 35,445 | 2/1997 | Pora ........................................ 206/532 |
| 191,607 | 6/1877 | Millard ..................................... 206/535 |
| 4,039,080 | 8/1977 | Cappuccilli . |
| 4,130,116 | 12/1978 | Cavazza ................................. 128/203 |
| 4,295,567 | 10/1981 | Knudsen . |
| 4,418,823 | 12/1983 | Romick ................................... 206/538 |
| 4,553,670 | 11/1985 | Collens . |
| 4,593,819 | 6/1986 | Will . |
| 4,736,849 | 4/1988 | Leonard et al. . |
| 4,828,113 | 5/1989 | Friedland et al. . |
| 4,889,238 | 12/1989 | Batchelor ............................... 206/535 |
| 4,890,741 | 1/1990 | Edelstein . |
| 5,002,048 | 3/1991 | Makiej, Jr. ......................... 128/200.23 |
| 5,007,419 | 4/1991 | Weinstein et al. ................. 128/200.23 |
| 5,181,189 | 1/1993 | Hafner . |
| 5,242,055 | 9/1993 | Pora ........................................ 206/532 |
| 5,363,842 | 11/1994 | Mishelevich et al. ............. 128/200.14 |
| 5,377,841 | 1/1995 | Varon . |
| 5,437,267 | 8/1995 | Weinstein et al. ................. 128/200.23 |
| 5,489,026 | 2/1996 | D'Aloia . |
| 5,489,027 | 2/1996 | Goerigk . |
| 5,522,380 | 6/1996 | Dwork ............................... 128/200.23 |
| 5,597,072 | 1/1997 | Lieberman et al. .................... 206/534 |
| 5,664,557 | 9/1997 | Makiej, Jr. ......................... 128/200.23 |
| 5,724,986 | 3/1998 | Jones, Jr. et al. ....................... 128/725 |
| 5,755,462 | 5/1998 | Lupi ........................................ 283/56 |
| 5,830,490 | 11/1998 | Weinstein et al. ..................... 424/405 |

FOREIGN PATENT DOCUMENTS

| 830269 | of 0000 | France . |
| 4301 282 A1 | of 0000 | Germany . |

OTHER PUBLICATIONS

Leape, et al., "Systems Analysis of Adverse Drug Events", *JAMA*, Jul. 5, 1995, vol. 274, No. 1, pp. 35–43.

Knox, Richard A., "Hospital Drugs Hurt 1 in 15", *The Boston Globe*, Jul. 5, 1995, vol. 248, No. 5, pp. 1 and 13.

Guest Editorial, "Building Partnerships with Patients", *Annals of Allergy, Asthma & Immunology*, Jan., 1997, vol. 78, pp. 1 & 4.

Kelloway, et al., "Comparison of Patients' Compliance with Prescribed Oral and Inhaled Asthma Medications", *Arch Intern Med.*, Jun. 27, 1997, vol. 154, pp. 1349–1352.

*Primary Examiner*—John G. Weiss
*Assistant Examiner*—Joseph F. Weiss, Jr.
*Attorney, Agent, or Firm*—Venable; George H. Spencer; Catherine M. Voorhees

[57] ABSTRACT

A method and device for organizing, storing, instructing, and coordinating the combined use of aerosol medications for the treatment of disorders including respiratory tract disorders for the purpose of reducing medication error and increasing therapeutic compliance.

41 Claims, 4 Drawing Sheets

METHOD AND DEVICE FOR ORGANIZING AND COORDINATING THE COMBINED USE OF TOPICAL AEROSOLS FOR THE TREATMENT OF RESPIRATORY DISORDERS

CROSS REFERENCES TO RELATED APPLICATIONS

The present invention is related to the co-pending application entitled "A Method and Device for Organizing and Coordinating the Combined Use of Topical Aerosols and Oral Medications for the Treatment of Disorders" (WNSTN 0016) filed Apr. 4, 1997, which is incorporated herein by reference.

BACKGROUND OF THE INVENTION

1. Field of Invention

The present invention relates to a method and device for organizing, storing, and coordinating the combined use of aerosol for the treatment of disorders including respiratory tract disorders for the purpose of reducing medication error and increasing therapeutic compliance.

2. Technical Review

Many drugs are utilized by patients over a period of time in varying amounts and in varying order to provide for their effective administration. Packaging has been developed for aiding the user of such drugs to comply with the proper administration over the proper time period. The dispensing apparatus associated with such multiple day administrative drugs are typically directed to the administration of pills or capsules, or similar solid medication.

U.S. Pat. No. 4,039,080, for example, discloses a tray having individual compartments for pills which may contain a week's medication with indicia indicating the day of the week and time of the day the medication is to be taken.

U.S. Pat. No. 4,553,670 discloses another device comprising a support on which are located two different ingestible medicinal substances in a single dose form with an adjacent portion for instructional information.

U.S. Pat. No. 4,593,819 discloses a covered pill tray of rectangular configuration having an array of open-topped compartments to hold a supply of medication arranged by the day and time of taking the medication.

U.S. Pat. No. 4,736,849 discloses a method and another type of dispenser for the storage and dispensing of calendar-oriented pills. U.S. Pat. No. 5,181,189 discloses a device for storage and time-regulated dispensing of drugs which includes a drug container to which is secured a signal generator.

U.S. Pat. No. 5,377,841 discloses a sleep therapy package which includes an audio recording of program material for inducing sleep, a card having a plurality of doses, some of which are medicine for inducing sleep and at least one of which is a placebo, along with patient instructions.

Cartonless packaging systems for containing liquids used, for example, as ophthalmic products, which also contain means for storing tablets and instructional material are disclosed in U.S. Pat. Nos. 5,489,026 and 5,489,027.

While the marketplace abounds with pill boxes and organizers for oral medications, no such organization tool is presently available for a lay person to organize individual aerosols together. Further, no pharmaceutically formulated device which combines aerosols together into a single organized treatment device with clear indicia and coordinated instructions is presently commercially marketed.

It is well known that ease of use is essential for medication compliance, and therefore for effective therapy. Multiple and variously configured individual aerosols are frequently prescribed to be used in conjunction with each other to comprise a treatment regimen for respiratory diseases. The technique of use, frequency of use, and number of actuations may be different for each. Their order of use may be important. It is noteworthy that a device to enhance ease of use and compliance with multiple aerosol medications, used together as a regimen, has been overlooked. The asthma death rate has notably increased in the United States in recent years, in part attributable to lack of patient compliance with multiple aerosol regimens. There is clearly a need for a method of reducing medication error and for enhancing therapeutic compliance of combined aerosol therapeutic regimens. It is therefore the object of the present invention to provide these devices and methods.

SUMMARY OF THE INVENTION

In accordance with the foregoing objectives, the present invention comprises a device for reducing medication error and enhancing therapeutic compliance of combined aerosols for treatment of disorders, such as respiratory disorders, comprising: (a) at least two topical multi-dosage aerosol medications; (b) indicia for distinguishing the medications; (c) instructions for coordination of the medications use together as a single therapeutic regimen; and (d) a unifying container. The present invention may also optionally include spacer devices to enhance the delivery of the aerosol spray and/or apparatus to measure outcomes of using the aerosol medications along with instructions for proper use. The present invention further comprises a method of reducing medication error and enhancing therapeutic compliance of combined topical medications for treatment of disorders, such as respiratory disorders, comprising the step of: utilizing a combined aerosol therapeutic regimen contained within such a unified device.

DETAILED DESCRIPTION OF THE PREFERRED EMBODIMENT

Figure 1:
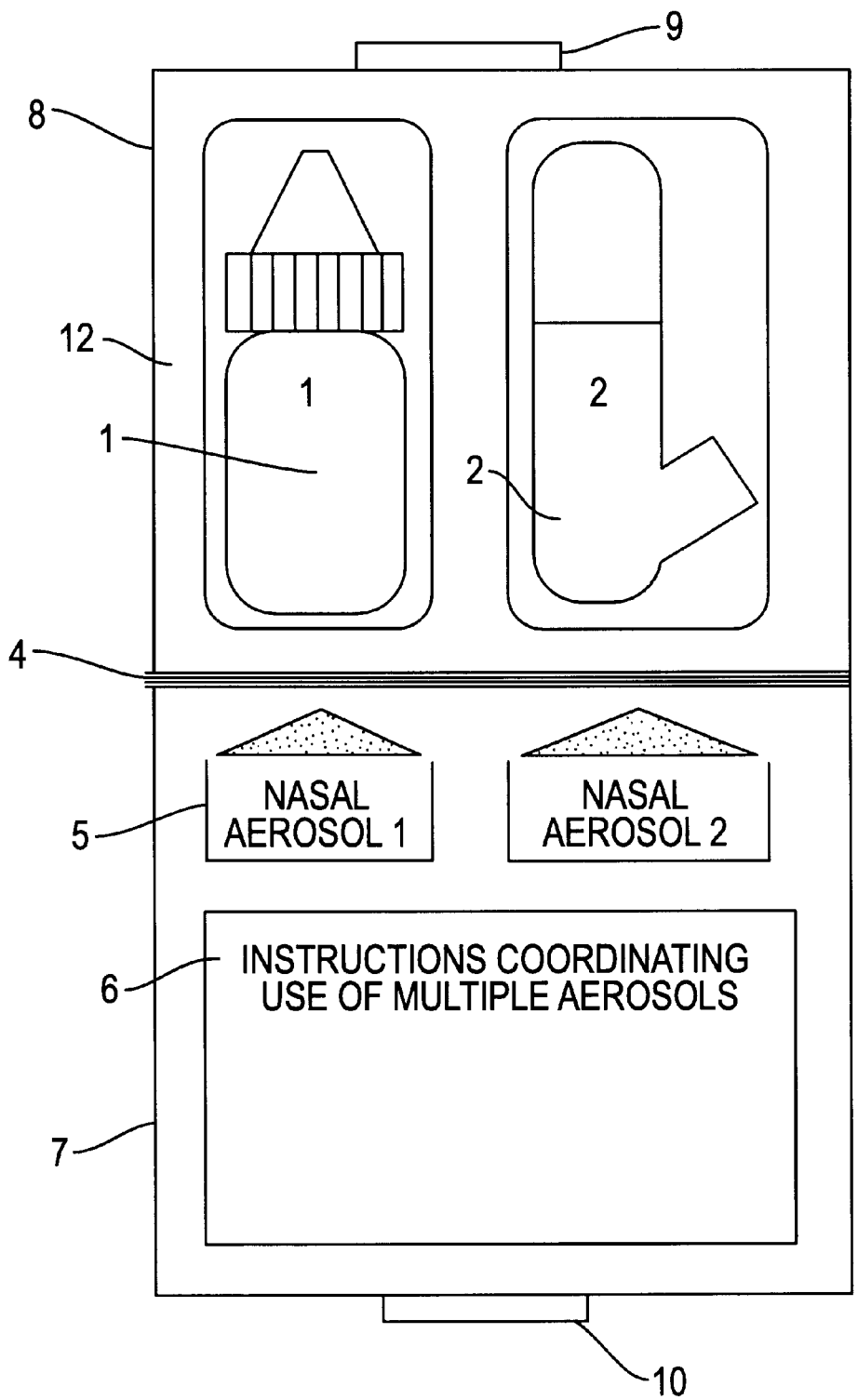
FIG. 1 is a plan view of a container in accordance with the present invention.

The following detailed description of the invention is provided to aid those skilled in the art in practicing the present invention. However, it should not be construed to unduly limit the present invention. Variations and modifications in the disclosed embodiments may be made by those of ordinary skill in the art without departing from the scope of the present inventive discovery.

The present invention provides a unifying dispensing container for medicaments for treatment of disorders requiring a combined topical medications regimen and a method for reducing medication error and enhancing therapeutic compliance of combined aerosols for treatment of such disorders. The unifying container holds at least two topical multi-dosage unit aerosol medications, indica for distinguishing these medications, and instructions for their coordinated use together as a single therapeutic regimen. Spacer devices and apparatus to measure outcomes of using the aerosol medications may also be included. It is to be understood that by multi-dosage aerosol unit it is meant that more than one dosage unit is available within the aerosol medication. The word aerosol encompasses its ordinary dictionary meaning of a suspension of fine solid or liquid particles in air or gas.

Referring to the drawings, it will be understood that while preferred embodiments of the invention have been illustrated and described, the invention is not limited to such embodiments. Changes and additions may be made therein and thereto without departing from the spirit of the invention.

Figure 2:
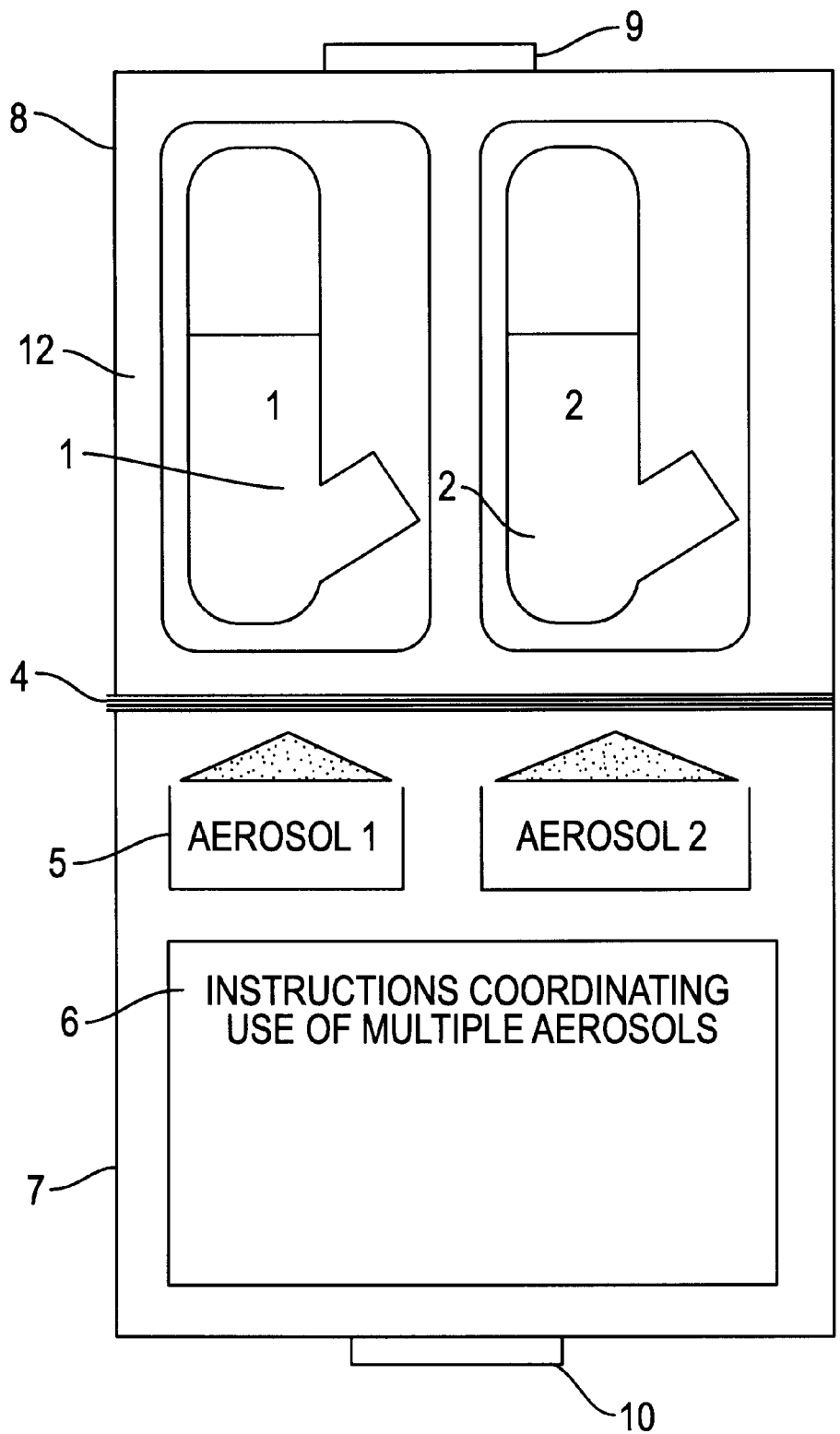
FIG. 2 is a plan view of another container in accordance with the present invention.
Figure 3:
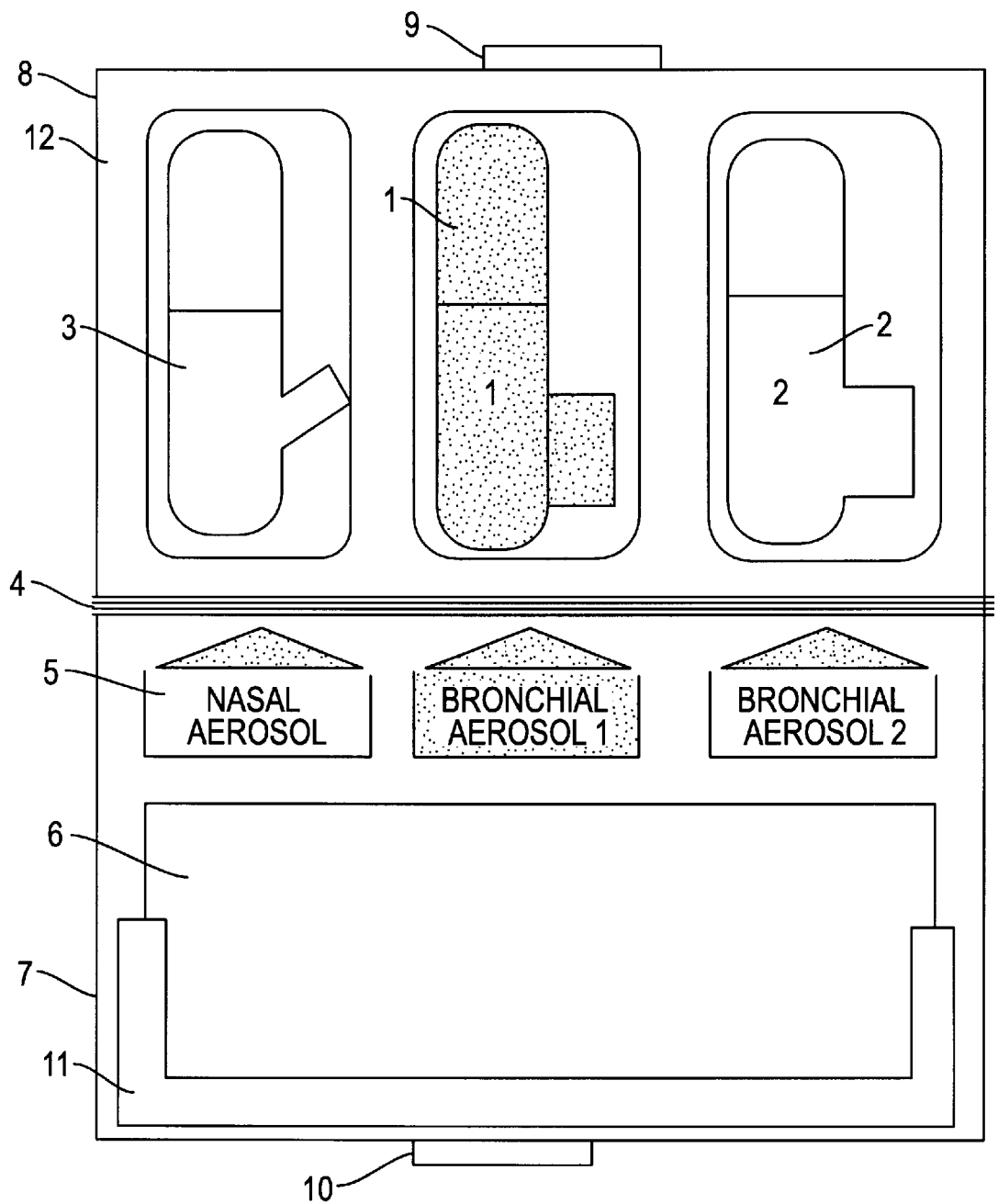
FIG. 3 is a plan view of a yet another container in accordance with the present invention for nasal and bronchial aerosol treatment.

Three embodiments of the unifying container of the present invention are respectively depicted in FIG. 1, FIG. 2 and FIG. 3. Referring to FIG. 1 and FIG. 2, a support package 12 which houses aerosols 1 and 2 is illustrated. A fold 4 in the package is provided in the center. Identifying indica 5 is provided directly under and aligned with each respective aerosol housing. An instruction bearing portion 6 provides instructions coordinating use of the aerosols. The instructions may be unalterable or may be capable of being altered yet maintained within the unifying container. The instruction bearing portion may also include an erasable pad or a pad with multiple blank tear off sheets. The lid portion 7 and the bottom portion 8 of the support package each contain respective clasp portions 9 and 10 which can be secured together when the support package is folded along fold 4. FIG. 3 shows a frame 11 to accommodate interchangeable instructions. FIG. 3 also depicts bronchial aerosols 1 and 2 along with nasal aerosol 3.

Figure 4:
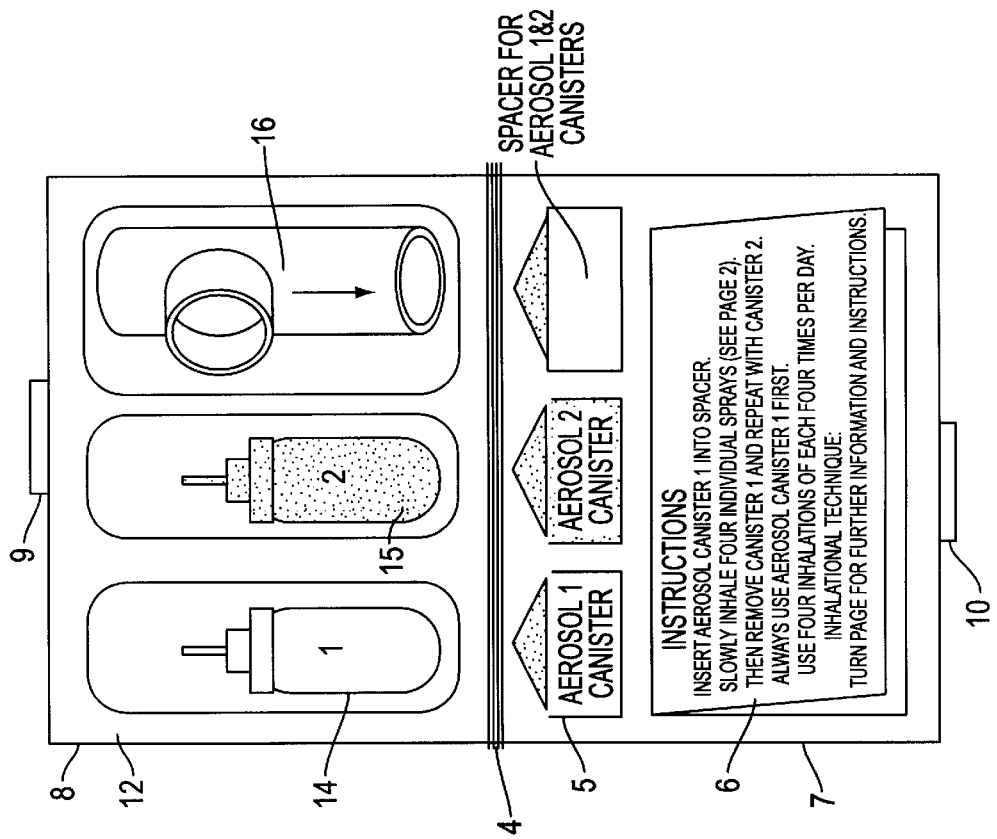
FIG. 4 depicts an embodiment of the invention with two bronchial aerosol units intended for coordinated use, and a simple spacer device which fits the outlets of both bronchial aerosol units. The instructions include directions for the proper use of the spacer device together with the bronchial aerosol units.
Figure 5:
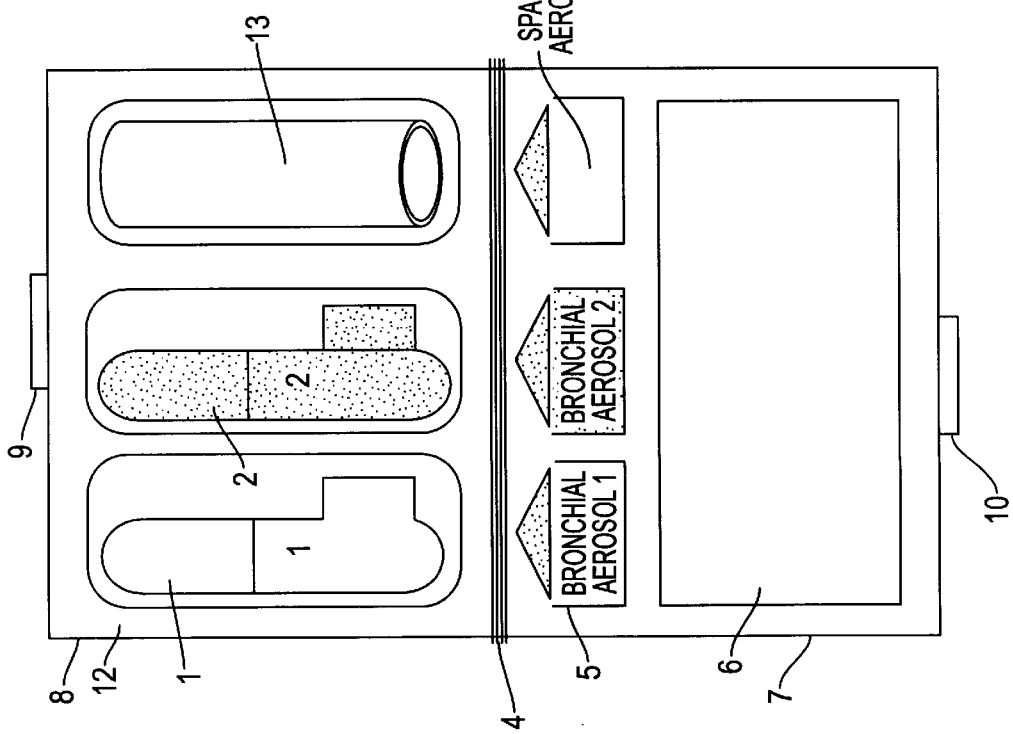
FIG. 5 depicts an embodiment of the invention with two bronchial aerosol canisters intended for coordinated use, and a spacer device which fits the outlets of the canisters. The instructions include directions for the proper use of the spacer device together with the bronchial aerosol canisters.

FIG. 4 and FIG. 5 depict two additional embodiments of the present invention which respectively contain spacer devices 13 and 16. FIG. 4 depicts a tubular spacer device 13. FIG. 5 depicts spacer device 16 which is a spacer for aerosol canisters 1 and 2. An arrow on spacer 16 indicates the direction of inhalational flow.

The packaging may be adapted in accordance with the requirements of the regimen by widening the packaging and increasing the number of housings and indicia. Additionally, the packaging may be in any geometric configuration and the containers may be any suitable pharmaceutical container.

Because the respiratory mucosa is structured as a conduit for air, it is possible to deliver medication topically to the respiratory mucosa by aerosol. Often it is advisable for individuals suffering from respiratory tract disorders such as rhinitis, bronchitis, or asthma to utilize a combination of aerosols as a treatment regimen. Treatment which necessitate a multiplicity of aerosol components poses a number of problems for patients. These multiple medication treatments may be a source of confusion and frustration which can result in medication error or lack of compliance.

Current treatment with a multiplicity of aerosol components lacks coordinating indicia and instructions being readily available to the patient for verifying the multiple component use together. Consequently, patients are confronted with a multiplicity of medications and may lose track of which medication is which. Individual components may be lost, misplaced, or ignored particularly so with instructions issued separately from the medication. Lacking organization, the least used, least immediate acting, or least obvious acting components, even if important and offering enhanced long-term effect, are the ones most likely to be lost or ignored. This is a particularly important consideration in asthma therapy. Inhaled corticosteroids offer no immediate relief for asthma, but reverse inflammation, the underlying disease process. Failure to comply with the recommended use of inhaled corticosteroids has been positively associated with increased morbidity and asthma deaths.

Furthermore, in spite of careful oral and written instruction from the health care provider, many patients are known to use what they have conveniently available. These haphazard applications can not only result in treatment failure, but also result in further expense for the patient who will eventually have to seek additional professional medical consultation involving additional medical personnel time and expense to instruct and organize therapy for these individuals. The devices and methods of the present invention would greatly help overcome these noted problems.

Additionally, cost factors, as well as outcomes, are now being carefully considered by medical groups. There is a definite need for devices and methods which would help patients be more cognizant of their proper medication treatment and therapy regiments. Such devices and methods would improve and ensure patient compliance. They would provide not only a means of further instruction but also provide an organizational tool which can save additional medical personnel expenditures. Successful therapy is less costly than unsuccessful treatment which eventuates in prolonged illness, multiple illnesses, multiple clinic visits, or hospitalizations.

Often, subjects using hand held inhalers for asthma or bronchitis (otherwise referred to as "metered dose inhalers" or "bronchial aerosols") fail to advantageously direct the stream of aerosol and do not receive the full dosage, or place the inhaler outlet well into the mouth resulting in an impacting of the particles on the buccal and/or pharyngeal mucosa rather than into the airway. For this reason, it is often considered advantageous to utilize a spacing device to enhance the delivery of aerosol to the bronchial tree when using hand held inhalers.

An example of such a device is a simple tube through which the aerosol is sprayed and which properly directs the spray and allows a mixing of aerosol particles with the inspired air resulting in deeper penetration of the medication into the airways. Albeit simple, dimensions of such a tube are important in achieving enhanced dispersion and deposition of aerosol. More elaborate devices which either attach to the mouthpieces of conventional hand held inhalers or to the aerosol canisters separated from the rest of the inhaler apparatus are also used and are well known in the art.

The present invention encompasses incorporation of spacer devices, when desired. Advantages of incorporating a spacer unit include: certainty of compatibility of spacer apparatus with the aerosol units, coordination of spacer units with aerosol units by unified instructions, and enhanced compliance because of simplicity, organization, and ready availability of all of the components of inhalational treatment. (Clearly, a spacer in a jacket pocket at work, and an inhaler in another coat at home are unlikely to be used together.)

One embodiment of the present invention comprises multiple inhalational medications for the treatment of respiratory tract disorders which are contained within a compact unifying container along with indicia for each medicament component and instructions for the coordination of the medications use together in a single therapeutic regimen. Other embodiments of the present invention additionally include at least one spacer device and instructions which include directions for the proper use of the spacer devices with the aerosol units. Furthermore, other embodiments of the present invention may include additional apparatus to measure treatment outcomes which might be incorporated into the package. Examples of such apparatus are a peak expiratory flow meter or a spirometer which measures other parameters of airway patency, along with instructions for the use of the metering device and coordination of its use with the medication regimen. The incorporation of such a device would allow the patient to monitor his or her respiratory status, would encourage compliance with the treatment regime and would provide a warning of impeding treatment failure in the case of lack of compliance. In the preferred embodiments, the inhalational medications, the indicia, the spacer, the peak flow meter, and the instructions are easily visible.

Topical aerosol medications which are presently in use for the treatment of rhinitis include: corticosteroids, which reduce inflammation of the nasal mucous membranes; decongestants, which constrict the nasal mucous membranes; cell stabilizers, which inhibit the release of symptom-causing mediators; antihistamines, which block the action of histamine released in allergic reactions; and anticholinergic agents, which dry nasal mucous membranes.

Topical aerosol medications which are currently used for the treatment of bronchial disorders such as bronchitis and asthma include: corticosteroids, which reduce inflammation of the bronchial mucous membranes; adrenergic agonists, which relax bronchial smooth muscle; cell stabilizers, which inhibit the release of symptom-causing mediators; and anticholinergic agents, which open and dry the bronchial tree.

The choice of medications and their use together is dependent on numerous considerations besides mechanism of action and risks of the individual medications, and include absorption, time of onset after dosing, rate of elimination, duration of action after dosing, therapeutic effect by virtue of combination, and side effects by virtue of combination. Medication error and misuse due to a multiplicity of medications pose an additional risk. Medical/pharmaceutical expertise is clearly required to formulate a treatment regime utilizing a combination of topical medications and appropriate instructions for use by a lay individual affected by respiratory disorders.

EXAMPLES

The invention will be further clarified by a consideration of the following examples, which are intended to be purely exemplary of the invention.

Example 1

Topical Intranasal Aerosols for the Treatment of Rhinitis

One beneficial treatment regime might include a topical intranasal decongestant followed by a topical intranasal corticosteroid. Topical intranasal decongestants are generally rapidly acting and may bring about immediate relief but may cause irritation over time. Topical intranasal corticosteroid generally act more slowly over days to weeks but tend to bring about more permanent relief. The use of the two topical agents, with decongestant first, and corticosteroid following is the preferable order of use, since the decongestant can improve nasal patency rapidly and allow the corticosteroid improved passage into the nose. Because relief immediately follows topical intranasal decongestant use, individuals might be included to ignore the use of the remainder of the regimen if they were not linked by package and instruction, with a resulting negative effect: rebound, overuse of decongestant, irritation and inflammation, a common outcome of the use of topical decongestant alone.

Medications exemplifying this regimen might be: Neo-Synepherine Nasal Spray® (phenyleprine hydrochloride) (decongestant) two sprays in each nostril four times a day; followed by Beconase Nasal Spray® (beclomethasone diproprionate) one spray in each nostril four times a day.

Example 2

Topical Bronchial Aerosol Medications Regimen for the Treatment of Bronchial Respiratory Disorders Another treatment regime might include a topical inhaled rapidly acting adrenergic agonist followed by a topical inhaled corticosteroid each having a separate mechanism of action. A preferred order of administration would be: inhaled adrenergic agent first, to provide rapid smooth muscle relaxation and bronchial dilatation allowing improved distribution of the secondly inhaled corticosteroid. This combination of medication has been commonly utilized and it is not uncommon for the more immediate acting medication, the inhaled adrenergic agent, to be most used and the corticosteroid ignored, although compliance with this regimen is more likely to bring about settling of inflammation and more prolonged relief. Keeping the components of the treatment regime together and physically organized with indicia and combined instructions provides convenience and organization, and promotes compliance with the treatment regimen with less confusion, less treatment errors and improved outcomes. Medications for this regimen may include: Ventolin Inhalation Aerosol® (albuterol, USP) (bronchodilator) inhale two sprays four times a day; followed by Beclovent Inhalational Aerosol® (belcomethasone, USP) (corticosteroid) inhale two sprays four times a day.

Example 3

Topical Medications Regimen for the Treatment of Rhinitis and Bronchial Respiratory Disorders Upper respiratory (nasal) and lower respiratory (bronchial) disorders frequently occur together. It is well established that bronchial disorders may not improve unless concomitant nasal disorders are adequately treated. For example, nasal polyps with consequent sinus congestion may coexist with asthma and perpetuate asthmatic symptoms. For this reason, a combination of topical medications may be indicated for rhinitis with nasal polyps and bronchial respiratory disorders. Such a combination might include nasal and bronchial aerosol devices. Medication for the regimen may include: Beconase Nasal Spray® (beclomethasone diproprionate) (corticosteroid) one spray in each nostril four times a day; and Ventolin Inhalation Aerosol® (albuterol, USP) (bronchodilator) inhale two sprays four times a day, followed by Beclovent Inhalational Aerosol® (beclomethasone, USP) (corticosteroid) inhale two sprays four times a day.

Other variations may occur to those skilled in the art which are within the scope of the invention as set forth in the appended claims. Those of skill in the art may also recognize modifications to these presently disclosed embodiments. These variations and modifications are meant to be covered by the spirit and scope of the present claims.

What is claimed is:

1. A prepackaged therapeutic device for reducing medication error and enhancing therapeutic compliance of combined topical treatments, comprising:
   (a) at least two topical multi-dosage aerosol medications;
   (b) instructions for coordination of the at least two medications for use together as a single therapeutic regimen, said coordinating instructions including frequency of dosing and number of applications at each time of dosing for said at least two medications;
   (c) a unifying container structured to provide specific placements for said aerosol medications and said coordinating instructions and having a surface; and
   (d) indicia on at least one of the surface of said container and the aerosol medications for distinguishing said medications.

2. The device of claim 1 further comprising at least one spacer device which when used in conjunction with an aerosol medication enhances delivery of the medication to the bronchial tree of a user.

3. The device of claim 1 for treatment of respiratory disorders wherein the aerosols are directed to respiratory mucosa.

4. The device of claim 3 wherein the topical aerosol medications are selected from the group consisting of corticosteroids, decongestants, antihistamines, cell stabilizers, broncho-dilating adrenergic agonists, and anticholinergic agents.

5. The device of claim 1 wherein the medications order of utilization is indicated by their placement within the container.

6. The device of claim 1 wherein the instructions can be altered yet maintained within the unifying container.

7. The device of claim 1 wherein the unifying container further comprises a frame for insertion of instruction sheets.

8. The device of claim 1 wherein the coordinating instructions further comprises an erasable pad or a pad with multiple blank tear-off sheets.

9. The device of claim 1 further comprising a device to measure the effectiveness on airway patency of using the medications.

10. The device of claim 9 wherein the device to measure the effectiveness is a peak flow meter or a spirometer which measures other parameters of airway patency.

11. The device of claim 2 further comprising a device to measure the effectiveness on airway patency of using the medications.

12. The device of claim 11 wherein the device to measure the effectiveness is a peak flow meter.

13. The prepackaged therapeutic device of claim 1, wherein the coordinating instructions are located on a surface of the container.

14. A prepackaged, medicament dispensing container for combined topical treatments, comprising:
   (a) at least two topical multi-dosage aerosol medications;
   (b) indicia on at least one of a surface of said container and the aerosol medications for distinguishing the medications; and
   (c) instructions for coordination of the medications for use together as a single therapeutic regimen, said instructions including frequency of dosing and number of applications at each time of dosing.

15. The container of claim 14 further comprising at least one spacer device which when used in conjunction with an aerosol medication enhances delivery of the medication to the bronchial tree of a user.

16. The container of claim 14 for treatment of respiratory disorders wherein the aerosols are directed to respiratory mucosa.

17. The container of claim 14 wherein the topical aerosol medications are selected from the group consisting of corticosteroids, decongestants, antihistamines, cell stabilizers, broncho-dilating adrenergic agonists, and anticholinergic agents.

18. The container of claim 14 wherein the medications order of utilization is indicated by their placement within the container.

19. The container of claim 14 wherein the instructions can be altered yet maintained within the unifying container.

20. The container of claim 14 further comprising a frame for insertion of instruction sheets.

21. The container of claim 14 wherein the coordinating instructions further comprises an erasable pad or a pad with multiple blank tear-off sheets.

22. The container of claim 14 further comprising a device to measure the effectiveness on airway patency of using the medications.

23. The container of claim 15 further comprising a device to measure the effectiveness on airway patency of using the medications.

24. The prepackaged medicament dispensing container of claim 14, wherein the coordinating instructions are located on a surface of the container.

25. A method of reducing medication error and enhancing therapeutic compliance of combined topical treatments, comprising the step of:
   utilizing a combined aerosols therapeutic regimen contained within a unified device, comprising:
   (a) at least two topical multi-dosage aerosol medications;
   (b) instructions for coordination of the at least two medications for use together as a single therapeutic regimen, said coordinating instructions including frequency of dosing and number of applications at each time of dosing for said at least two medications;
   (c) a unifying container structured to provide specific placements for said aerosol medications and said coordinating instructions and having a surface; and
   (d) indicia on at least one of the surface of said unifying container and the aerosol medications for distinguishing said medications.

26. The method of claim 25 wherein the unified device further comprises at least one spacer device which when used in conjunction with an aerosol medication enhances delivery of the medication to the bronchial tree of a user.

27. The method of claim 25 for treatment of respiratory disorders wherein the aerosols are directed to respiratory mucosa.

28. The method of claim 25 wherein the topical aerosol medications are selected from the group consisting of corticosteroids, decongestants, antihistamines, cell stabilizers, broncho-dilating adrenergic agonists, and anticholinergic agents.

29. The method of claim 25 wherein the medications order of utilization is indicated by their placement within the container.

30. The method of claim 25 wherein the instructions can be altered yet maintained within the unifying container.

31. The method of claim 25 wherein the unified device further comprises a device to measure the effectiveness on airway patency of using the medications.

32. The method of claim 26 wherein the unified device further comprises a device to measure the effectiveness on airway patency of using the medication.

33. A method of reducing medication error and enhancing therapeutic compliance of combined topical treatments, comprising the steps of:

(a) obtaining a unified device comprising:
  at least two topical multi-dosage aerosol medications;
  instructions for coordination of the at least two medications for use together as a single therapeutic regimen, said coordinating instructions including frequency of dosing and number of applications at each time of dosing for said at least two medications;
  a unifying container structured to provide specific placements for said aerosol medications and said coordinating instructions and having a surface; and
  indicia on at least one of the surface of said container and the aerosol medications for distinguishing said medications;

(b) reviewing the coordinating instructions for coordination of aerosol medications used together as a single therapeutic regimen;

(c) reviewing the indicia for distinguishing the medications;

(d) selecting the appropriate aerosol medications as indicated by the indicia and the coordinating instructions; and (e) utilizing the medications as instructed by the coordinating instructions.

34. The method of claim 33 wherein the unified device further comprises at least one spacer device which when used in conjunction with an aerosol medication enhances delivery of the medication to the bronchial tree of a user.

35. The method of claim 33 wherein the unified device further comprises a device to measure the effectiveness on airway patency of using the medications.

36. The method of claim 33 wherein the unified device further comprises at least one spacer device and a device to measure the effectiveness on airway patency of using the medications.

37. A prepackaged unitary dispenser for organizing, storing, instructing, and dispensing topical medicament regimens and enhancing patient compliance, comprising:

(a) at least two aerosol medication containing enclosures, each enclosure enclosing one of at least two expertly selected aerosol medications;

(b) respective indicia for distinguishing the enclosed medications, said indicia being on at least one of the enclosed medications and on a surface of the unitary dispenser; and (c) expertly formulated instructions for coordination of the medications used together as a single therapeutic regimen, said coordinating instructions including frequency of dosing and number of applications at each time of a dosing and coordinating the use of said at least two aerosol mediation enclosures as a regimen.

38. The unitary dispenser of claim 37 further comprising at least one spacer device enclosure which when used in conjunction with an aerosol medication enhances delivery of the medication to the bronchial tree of a user.

39. The unitary dispenser of claim 37 further comprising an enclosure for a device to measure the effectiveness on airway patency of using the medications.

40. The unitary dispenser of claim 38 further comprising an enclosure for a device to measure the effectiveness on airway patency of using the medications.

41. The prepackaged unitary dispenser of claim 37 wherein, the coordinating instructions are located on a surface of the container.

* * * * *